United States Patent [19]

Outlaw et al.

[11] Patent Number: 4,516,435
[45] Date of Patent: May 14, 1985

[54] PRECISION MANIPULATOR HEATING AND COOLING APPARATUS FOR USE IN UHV SYSTEMS WITH SAMPLE TRANSFER CAPABILITY

[75] Inventors: Ronald A. Outlaw, Newport News; Bill T. Baugh, Poquoson, both of Va.

[73] Assignee: The United States of America as represented by the United States National Aeronautics and Space Administration, Washington, D.C.

[21] Appl. No.: 547,176

[22] Filed: Oct. 31, 1983

[51] Int. Cl.³ .................. G01N 1/00; G01N 37/00
[52] U.S. Cl. .................. 73/863.11; 73/864.81; 219/201; 219/221; 219/285; 414/217
[58] Field of Search .......... 73/863.11, 863.85, 864.81, 73/864.83, 864.91; 414/217; 250/288; 219/201, 221, 243, 385; 374/12, 14

[56] References Cited

U.S. PATENT DOCUMENTS

| | | | |
|---|---|---|---|
| 3,055,206 | 9/1962 | Watson et al. | 374/14 |
| 3,189,494 | 6/1965 | Short | 219/385 |
| 3,586,488 | 6/1971 | Trevalion et al. | 73/863.85 |
| 3,732,722 | 5/1973 | Norem et al. | 374/12 |
| 4,045,860 | 9/1983 | Brunnee et al. | 250/288 |
| 4,412,771 | 11/1983 | Gerlach et al. | 414/217 |

Primary Examiner—S. Clement Swisher
Attorney, Agent, or Firm—Howard J. Osborn; John R. Manning; William H. King

[57] ABSTRACT

An improvement of a precision manipulator for use in UHV systems with sample transfer capability in which a spring loaded thermocouple 47 and a heater electrode (51, 52) are both in direct contact with the transferred sample 35. The thermocouple and heater electrode assembly are mounted concentric with a sample receiving block 33 on the end of an offset manipulator 20. Hence, when a sample is transferred from an introduction chamber 12 into the UHV chamber 11, it contacts the spring loaded thermocouple 47 and then seats a heater electrode 52. Cooling by a copper plate 41 and a strap 22 combined with the resistance heating capability allow sample temperatures over the range of 150°–1750° K. while positioned in front of any diagnostic instrument in the UHV system and while taking data with these instruments.

6 Claims, 3 Drawing Figures

PRECISION MANIPULATOR HEATING AND COOLING APPARATUS FOR USE IN UHV SYSTEMS WITH SAMPLE TRANSFER CAPABILITY

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

The invention relates generally to ultra-thin vacuum (UHV) systems with sample transfer capability and more specifically concerns improvements of a manipulator in a UHV sample transfer system.

Numerous laboratories have reported their versions of UHV sample transfer systems that, in most cases, have been retrofitted to existing equipment. A. R. Schlier, *Journal of Vacuum Science Technology*, Vol. 20, p. 100, 1982, R. S. Polzotti and J. A. Schwarz, *Journal of Vacuum Science Technology*, Vol 17, p. 655; 1980; B. J. Mulder, *Journal of Phys. E. Scientific Instruments*, Vol 12, p. 908, 1979; R. E. Clausing, L. Heatherly, and L. C. Emerson, *Journal of Vacuum Science Technology*, Vol. 16, p. 708, 1979; C. A. Crider, G. Cisneros, P. Mark and J. D. Levine, *Journal of Vacuum Science Technology*, Vol. 13, p. 1202, 1976. These systems have proven to be relatively inexpensive as well as quite versatile. However, one of the more difficult requirements for these assemblies is the sample transfer to precision manipulators that can heat and cool over a wide temperature range, while simultaneously making accurate temperature measurements over the full range of temperatures and manipulator positions.

It is the primary object of this invention to provide an improved manipulator with heating and cooling capability for use in UHV systems compatible with sample transfer.

Another object of this invention is to provide an added capability for precision manipulators used in UHV systems with sample transfer to heat and cool over a wide temperature range, while simultaneously making accurate temperature measurements over the full range of temperatures and manipulator positions.

A further object of this invention is to provide a manipulator that allows complete sample transfer by a rotating, translating transfer arm.

A still further object of this invention is to provide a manipulator in which the temperature of the transferred sample is measured by a thermocouple that makes direct contact with the sample.

Other objects and advantages of this invention will become apparent hereinafter in the specification and drawings.

SUMMARY OF THE INVENTION

The invention is an improved manipulator for UHV systems equipped with sample transfer capability. A sample holder with a sample attached is coupled into the manipulator and makes electrical contact with a rear electrode assembly that has a thermocouple and a heater electrode included. The thermocouple, which comes in contact with the sample first, is spring loaded thereby allowing the sample to push the thermocouple back and then make contact with the heater electrode as the sample holder is further inserted into the manipulator. The front plate of the manipulator, into which the sample holder is secured, has a flexible cooling strap attached to it for cooling the sample.

DETAILED DESCRIPTION OF THE INVENTION

Figure 1:
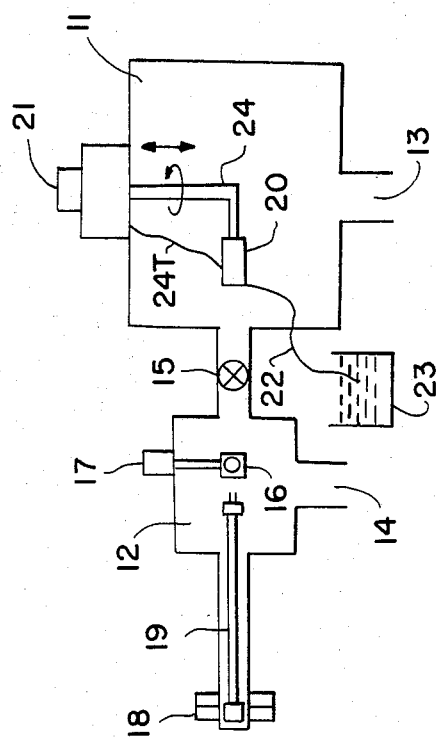
FIG. 1 is a schematic drawing of a UHV system with sample transfer capability in which the present invention can be used.

The sample transfer systems shown in FIG. 1 includes a UHV chamber with numerous diagnostic instruments 11 and a sample introduction vacuum chamber 12 where samples are selected for testing in chamber 11. Chambers 11 and 12 have pumping ports 13 and 14, respectively, which are connected to various vacuum pumps. An isolation valve 15 is located between the two chambers. A carrousel 16 holds several samples to be tested. A control mechanism 17 controls the position of carrousel 16 inside chamber 12. A magnetic control device 18 positions and rotates a transfer rod 19. A manipulator 20 located inside chamber 11 is positioned by a control mechanism 21 to receive the sample on transfer rod 19 and then to position the received sample in front of testing devices (not shown). Manipulator shafts 24 serve also as electrical conductors for heating the sample. The thermocouple wires 24T for measuring the temperature of the sample are connected to one of the manipulator feed throughs. A flexible copper cooling strap 22 is attached to the face of the receiving block on manipulator 20 and extends outside of chamber 11 into a container 23 of liquid nitrogen to provide cooling of the sample.

In the operation of the sample transfer system shown in FIG. 1, with carrousel 16 in the position shown, the position of transfer rod 19 is controlled by control device 18 to remove a sample from the carrousel. Then carrousel 16 is moved out of the path of transfer rod 19 and valve 15 is opened. Transfer rod 19 is moved into chamber 11 and attaches the sample to manipulator 20, the transfer rod is withdrawn from chamber 11 and valve 15 is closed. The sample is then ready for testing.

Figure 3:
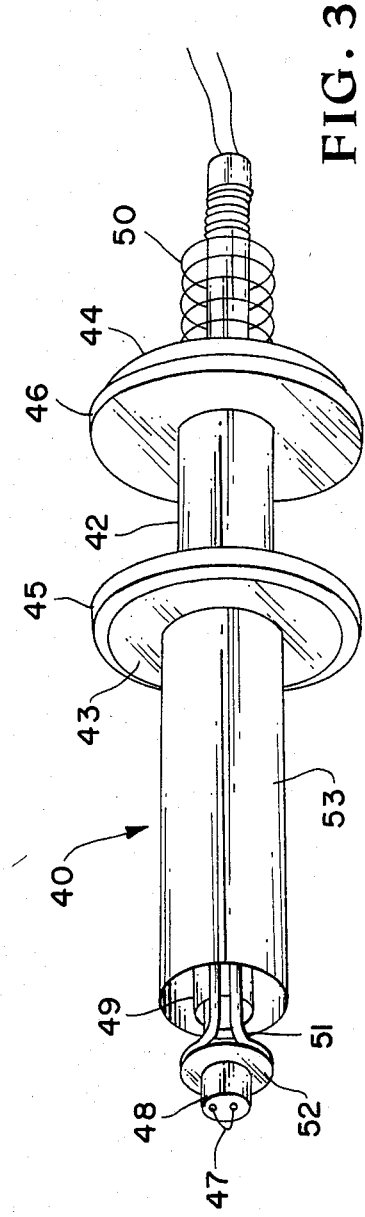
FIG. 3 is a drawing of the rear electrode assembly shown in FIG. 2.
Figure 2:
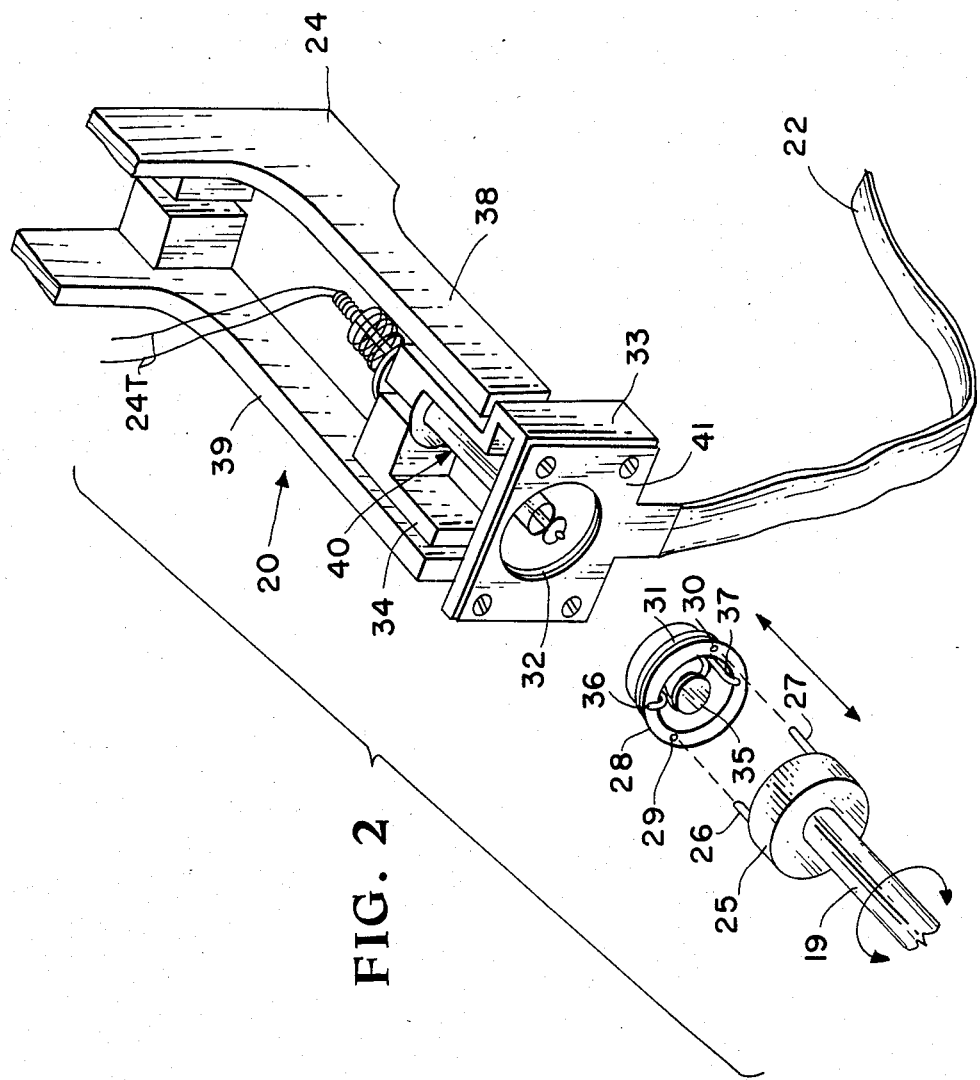
FIG. 2 is a drawing of the present invention.

Turning now to the embodiment of the invention selected for illustration in FIG. 2 of the drawings, the transfer rod 19 and manipulator 20 are shown in more detail than in FIG. 1. Transfer rod 19 includes a head 25 including two pins, 26 and 27, extending therefrom for attachment to an electrically conductive sample holder 28. Two holes, 29 and 30, are in sample holder 28 for engaging pins 26 and 27, respectively, and thereby attaching sample holder 28 to the end of transfer rod 19. As stated in the Summary of the Invention, the sample holder 28 is secured to the manipulator 20 in any suitable manner. Threads 31 are formed on the sample holder 28 for screwing into a threaded opening 32 in the face of a receiving block 33 of manipulator 20. Other known means are available for effecting the connection of the sample holder 28 to the manipulator 20 and the threaded coupling is shown only for illustrative purposes. Various types of other connections such as snap fittings, channel and lock couplings, etc. may be used. A sample 35 with heater wires 36 and 37 attached to the sample are inserted into sample holder 28 such that both wires make electrical contact with sample holder 28. Manipulator 20 includes electrodes 38 and 39 with a flip mechanism 34 mounted between the two electrodes. The two sides of flip mechanism 34 are electrically isolated from the other with electrode 38 electrically connected to the right side and with electrode 39 electrically connected to the left side. A rear electrode assembly 40, shown in FIG. 3, is mounted between the two sides of flip mechanism 34. The right side of flip mechanism 34 is integral with the receiving block 33. A copper plate 41 which has the cooling strap 22 attached to it is attached to the face of receiving block 33.

The rear electrode assembly 40, as shown in FIG. 3, includes a mounting shaft 42 and base plates 43 and 44 for mounting the assembly in the manipulator. Insulating spacers 45 and 46 are located between the base plates 43 and 44. A thermocouple 47 encased by an alumina (ceramic) thermocouple sheath 48 extends through mounting shaft 42. Sheath 48 is slidably mounted inside a tube 49 that is mounted inside mounting shaft 42. A spring 50 has one of its ends suitably attached to sheath 48 and its other end attached to base plate 44. A heater electrode 51 surrounds sheath 48 and is tack welded to mounting shaft 42 where it is electrically connected through mounting shaft 42 to manipulator shaft 39. A ring electrode 52 is included on the end of heater electrode 51 to make a uniform connection with the sample. A radiation shield 53 covers tube 49 and heater electrode 51.

In the operation of this invention, whenever sample holder 28 is screwed into receiving block 33, sample 35 will first come in contact with thermocouple 47. Then as sample holder 28 is further screwed into receiving block 33, sheath 48 will be pushed back against spring 50 until the sample makes contact with ring electrode 52 at which time thermocouple 47 and electrode 52 are both in contact with sample 35. The direct contact of the thermocouple with the sample is very important since it eliminates having to know the emissivity and size of the sample. They can differ with each new sample installed, thus requiring a direct measurement of temperature with each experiment. In addition of the thermocouple being in compression on the back of the sample, the rotation of the sample enhances the intimate contact made by the thermocouple to the sample. Cooling of the sample is accomplished by the flow of heat from sample 35 through wires 36 and 37, sample holder 28, plate 41, cooling strap 22 into the container of liquid nitrogen 23.

The advantages of this invention are that it provides an inexpensive improved manipulator in a UHV system with sample transfer capability that can heat and cool over a wide temperature range (150°1750° K.) while simultaneously making accurate temperature measurements over the full range of temperatures and manipulator positions, it provides for direct contact with the sample by the thermocouple and the heating element, it provides for cooling of the sample through a plate on the receiving block and a cooling strap and it provides for transferring the sample from the transfer rod to the receiving block by simple translation and rotation and the subsequent retraction of the transfer rod and closure of the isolation valve. This permits minimum compromise of the UHV conditions.

It is to be understood that the form of the invention herewith shown and described is to be taken as a preferred embodiment. Various changes may be made without departing from the invention. For example, the improved manipulator can be used in sample transfer systems different from the one disclosed.

What is claimed is:

1. A precision manipulator for use in a UHV system with sample transfer capability comprising:
   an electrically conductive sample holder;
   means for mounting a sample on said sample holder such that heating current will flow from the sample to said sample holder;
   first and second manipulator electrodes;
   a receiving block electrically connected to said first manipulator electrode and with an opening through it such that said sample holder will fit into the receiving block;
   means for attaching said sample holder to said receiving block whenever the sample holder is moved into the receiving block;
   a rear electrode assembly including a heater electrode fixed relative to said rear electrode assembly and a thermocouple; and
   means for spring loading said thermocouple such that when a pressure is exerted against said thermocouple the thermocouple will move relative to said rear electrode assembly;
   said rear electrode assembly mounted with said heater electrode electrically connected to said second manipulator electrode, said heater electrode and said thermocouple mounted in said rear electrode assembly behind said opening in said receiving block such that when said sample holder is moved into said receiving block said sample comes in contact with said thermocouple first and then as said sample holder is further moved into said receiving block the thermocouple is pushed back against said spring loading means until said sample makes contact with said heater electrode at which time the thermocouple and the heater electrode are both in contact with said sample.

2. A precision manipulator according to claim 1 wherein said means for mounting a sample in said sample holder is two wires with each wire attached to said sample and in contact with said sample holder.

3. A precision manipulator according to claim 1 including a heat conducting plate on the face of said receiving block and a flexible cooling strap attached to said heat conducting plate to provide means for cooling said sample.

4. A precision manipulator according to claim 1 wherein said means for attaching said sample holder to said receiving block is threads on the sample holder and in the opening of said receiving block.

5. A precision manipulator according to claim 4 wherein said sample holder includes means for mating with a transfer rod such that when the transfer rod is rotated the sample holder can be screwed into or out of said receiving block.

6. A precision manipulator according to claim 1 wherein said means for spring loading said thermocouple includes an elongated holder for said thermocouple with the thermocouple extending beyond one end of said holder, said holder slidably mounted on said rear electrode assembly, and a spring with one end attached to said holder and a second end attached to said rear electrode assembly whereby whenever a pressure is exerted against said thermocouple the holder will move relative to said rear electrode assembly until the sample makes contact with said heater electrode and said spring will hold the thermocouple in contact with said sample.

* * * * *